(12) United States Patent
Lubisch et al.

(10) Patent No.: US 6,380,220 B1
(45) Date of Patent: Apr. 30, 2002

(54) DERIVATIVES FROM PIPERIDINE-KETO ACID, THEIR PREPARATION AND USE

(75) Inventors: Wilfried Lubisch, Mannheim; Achim Möller, Grünstadt; Jürgen Delzer, Speyer, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/284,543

(22) PCT Filed: Sep. 23, 1997

(86) PCT No.: PCT/EP97/05202

§ 371 Date: Apr. 14, 1999

§ 102(e) Date: Apr. 14, 1999

(87) PCT Pub. No.: WO98/16512

PCT Pub. Date: Apr. 23, 1998

(30) Foreign Application Priority Data

Oct. 15, 1996 (DE) .......................... 196 42 591

(51) Int. Cl.$^7$ .................. A61K 31/445; C07D 211/46
(52) U.S. Cl. .................. 514/330; 514/235.5; 514/314; 514/318; 514/319; 514/324; 544/129; 546/176; 546/194; 546/202; 546/205; 546/209; 546/226; 546/227
(58) Field of Search .............. 514/235.5, 314, 514/318, 319, 324, 330; 544/129; 546/176, 194, 202, 205, 209–226, 227

(56) References Cited

U.S. PATENT DOCUMENTS 5,541,290 A * 7/1996 Harbeson et al. ........... 530/330

FOREIGN PATENT DOCUMENTS

| EP | 520 336 | 12/1992 |
| WO | 92/11850 | 7/1992 |
| WO | 92/12140 | 7/1992 |
| WO | 94/00095 | 1/1994 |
| WO | 95/00535 | 1/1995 |

OTHER PUBLICATIONS

Takagaki et al. "Inhibition of ischemia induced fodrin . . . " J. Neurochem. v.68, p.2507–2513, 1997.*

* cited by examiner

Primary Examiner—Ceila Chang
(74) Attorney, Agent, or Firm—Keil & Weinkauf

(57) ABSTRACT

Piperidineketocarboxylic acid derivatives of the general formula I

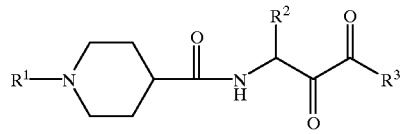

and their tautomeric and isomeric forms, and physiologically tolerable salts thereof, where the variables have the meanings given in the description, preparation of these compounds and their use as drugs.

10 Claims, No Drawings

DERIVATIVES FROM PIPERIDINE-KETO ACID, THEIR PREPARATION AND USE

This application is a 371 of PCT/EP97/05202 titled Sep. 23, 1997.

The present invention relates to novel ketoesters and ketoamides which are inhibitors of enzymes, in particular cysteine proteases, such as calpain (=calcium-dependant cysteine protease and its isoenzymes and cathepsins, for example B and L.

Calpains are intracellular, proteolytic enzymes from the cysteine proteases group and are found in many cells. The enzyme calpain is activated by increased calcium concentration, a differentiation being made between calpain I or μ-calpain, which is activated by μ-molar concentrations of calcium ions, and calpain II or m-calpain, which is activated by m-molar concentrations of calcium ions (P. Johnson, Int. J. Biochem. 1990, 22(8), 811–22). Today, still further calpain isoenzymes are postulated (K. Suzuki et al., Biol. Chem. Hoppe-Seyler, 1995, 376(9), 523–9).

It is suspected that calpains play an important part in various physiological processes. These include cleavages of regulatory proteins such as protein kinase C, cytoskeletal proteins such as MAP 2 and spectrin, muscle proteins, protein degradation in rheumatoid arthritis, proteins in the activation of platelets, neuropeptide metabolism, proteins in mitosis and others, which are mentioned in M. J. Barrett et al., Life Sci. 1991, 48, 1659–69 and K. K. Wang et al., Trends in Pharmacol. Sci., 1994, 15, 412–9.

Increased calpain levels were measured in various pathophysiological processes, for example: ischemias of the heart (eg. cardiac infarcts), of the kidney or the central nervous system (eg. stroke), inflammation, muscular dystrophy, cataracts of the eyes, injuries to the central nervous system (eg. trauma), Alzheimer's disease etc. (see K. K. Wang, above). A relationship of these diseases with increased and lasting intracellular calcium levels is presumed. As a result, calcium-dependent processes are overactivated and no longer subjected to physiological regulation. Accordingly, overactivation of calpains can also trigger pathophysiological processes.

It was therefore postulated that inhibitors of the calpain enzymes may be useful for the treatment of these diseases. Various investigations confirm this. Thus Seung-Chyul Hong et al., Stroke 1994, 25(3), 663–9 and R. T. Bartus et al., Neurological Res. 1995, 17, 249–58 have shown a neuroprotective action of calpain inhibitors in acute neurodegenerative disorders, such as occur after stroke. Likewise, after experimental cerebral traumas, calpain inhibitors improved the recovery from the memory power deficits and neuromotor disorders occurring (K. E. Saatman et al. Proc. Natl. Acad. Sci. USA, 1996, 93, 3428–3433). C. L. Edelstein et al., Proc. Natl. Acad. Sci. USA, 1995, 92, 7662–6, found a protective action of calpain inhibitors on kidneys damaged by hypoxia. Yoshida, Ken Ischi et al., Jap. Circ. J. 1995, 59(1), 40–8, were able to show favorable effects of calpain inhibitors after cardiac damage which was produced by ischemia or reperfusion. Since calpain inhibitors inhibit the release of the β-AP4 protein, a potential use as a therapeutic for Alzheimer's disease was proposed (J. Higaki et al., Neuron, 1995, 14, 651–59). The release of interleukin-1α is likewise inhibited by calpain inhibitors (N. Watanabe et al., Cytokine 1994, 6(6), 597–601). It was furthermore found that calpain inhibitors show cytotoxic effects on tumor cells (E. Shiba et al. 20th Meeting Int. Ass. Breast Cancer Res., Sendai Jp, 1994, 25.–28. Sept., Int. J. Oncol. 5(Suppl.), 1994, 381).

Further possible uses of calpain inhibitors are mentioned in K. K. Wang, Trends in Pharmacol. Sci., 1994, 15, 412–9.

Calpain inhibitors have already been described in the literature. Mainly, however, these are either irreversible or peptide inhibitors. As a rule, irreversible inhibitors are alkylating substances and have the disadvantage that they have an unselective reaction in the body or are unstable. Thus these inhibitors often show undesired side effects, such as toxicity, and are then restricted in their use or unutilizable. Among the irreversible inhibitors can be counted, for example, the epoxides E 64 (E. B. McGowan et al., Biochem. Biophys. Res. Commun. 1989, 158, 432–5), α-haloketones (H. Angliker et al., J. Med. Chem. 1992, 35, 216–20) or disulfides (R. Matsueda et al., Chem. Lett. 1990, 191–194).

Many known reversible inhibitors of cysteine proteases such as calpain are peptide aldehydes, in particular dipeptide and tripeptide aldehydes such as, for example, Z-Val-Phe-H (MDL 28170) (S. Mehdi, Trends in Biol. Sci. 1991, 16, 150–3) and the compounds from EP 520336. Under physiological conditions, peptide aldehydes have the disadvantage that they are often unstable on account of the great reactivity, can be rapidly metabolized and are prone to nonspecific reactions which can be the cause of toxic effects (J. A. Fehrentz and B. Castro, Synthesis 1983, 676–78). The use of peptide aldehydes in the treatment of diseases is thus restricted or ineffective. It is thus surprising that only a few aldehydes can be employed as active compounds, namely especially when the aldehyde group is stabilized, for example by hemiacetal formation.

An advance is the discovery that certain peptide ketone derivatives are also inhibitors of cysteine proteases and, in particular, calpain. Thus in the case of serine proteases for example, ketone derivatives are known as inhibitors, the keto group being activated by an electron-withdrawing group such as $CF_3$. In the case of cysteine proteases, derivatives with ketones activated by $CF_3$ or similar groups are less active or inactive (M. R. Angelastro et al., J. Med. Chem. 1990, 33, 11–13). Surprisingly, in the case of calpain, until now only ketone derivatives in which on the one hand α-position leaving groups cause an irreversible inhibition and on the other hand a carboxylic acid derivative activates the keto group, were found as active inhibitors (see M. R. Angelastro et al., see above; WO 92/11850; WO 92,12140; WO 94/00095 and WO 95/00535). However, of these ketoamides and ketoesters, only peptide derivatives have previously been described as active (Zhaozhao Li et al., J. Med. Chem. 1993, 36, 3472–80; S. L. Harbenson et al., J. Med. Chem. 1994, 37, 2918–29 and see above M. R. Angelastro et al.).

It is an object of the present invention to make available nonpeptide inhibitors which are derived from the more stable ketones and which do not have the general problems of peptides, (metabolic stability, difficulty in getting through the cell membranes etc.).

The present invention relates to piperidineketocarboxylic acid derivatives of the formula I

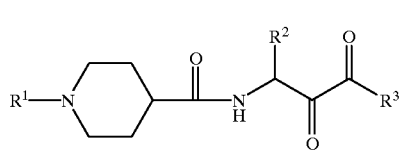

I and their tautomeric and isomeric forms, and possible physiologically tolerable salts, where the variables have the following meanings:

$R^1$ is —CO—$R^4$, —$SO^2$—$R^4$, —CONH—$R^4$, COOR$^4$, —C(=N)—$R^4$, —C(=O) —NHR$^4$ and —C(=S)—NHR$^4$;

$R^2$ is —$C_1$–$C_6$-alkyl, which is branched or unbranched and can additionally carry a phenyl, pyridine or naphthyl ring which in turn can be substituted by at most two radicals $R^5$, it being possible for $R^5$ to be $C_1$–$C_4$-alkyl which is branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCOPh, —$NHSO_2$—$C_1$–$C_4$-alkyl, $NHSO_2$—Ph, —$SO_2$—$C_1$–$C_4$-alkyl and —$SO_2$Ph;

$R^3$ is —$OR_6$ or —$NHR^6$;

$R^4$ is —$C_1$–$C_6$-alkyl which is branched or unbranched, it also being possible for a chain of two or more C atoms to contain a double bond or triple bond and to be substituted by one or two rings such as phenyl, naphthalene, quinoxaline, quinoline, isoquinoline, pyridine, thiophene, benzothiophene, benzofuran, pyrimidine, thiazole, isothiazole, triazole, imidazole, cyclohexyl, cyclopentyl, fluorene, indole, benzimidazole, oxazole, isooxazole and furan, it being possible for each of the rings themselves additionally to carry at most two radicals $R^5$;

$R^6$ is hydrogen, a phenyl ring which can additionally carry one or two radicals $R^5$, $C_1$–$C_6$-alkyl which is branched or unbranched and can contain a double bond or a triple bond, and a ring such as phenyl, naphthalene, pyridine, pyrimidine, piperidine, pyrrolidine, morpholine, thiophene, quinoline and isoquinoline, it being possible for the aromatic rings additionally to carry at most two radicals —$NR^7R^8$ or $R^5$, it being possible for $R^7$ and $R^8$ independently of one another to be hydrogen or $C_1$–$C_6$-alkyl which is branched or unbranched.

Preferred piperidineketocarboxylic acid derivatives of the general formula I are those as claimed in claim 2, for which $R^1$ is —C(=O)$R^4$, —$SO_2R^4$, $R^2$ is $C_1$–$C_6$-alkyl which is branched or unbranched, —$CH_2$—Ph or —$CH_2$-pyridyl, $R^3$ is —$OR^6$ or —$NHR^6$ and $R^4$, $R^5$ and $R^6$ have the meanings as set forth in claim 2.

Particularly preferred piperidineketocarboxylic acid derivatives of the general formula I are those as claimed in claim 3, for which $R^1$ is —C(=O)$R^4$, —$SO_2R^4$, $R^2$ is —$C_1$–$C_4$-alkyl or —$CH_2$—Ph, $R^3$ is —$NHR^6$, $R^4$ is —CH=CH—$R^9$, it being possible for $R^9$ to be phenyl, naphthalene or quinoline, and $R^6$ is hydrogen, $C_1$–$C_4$-alkyl which can be substituted by phenyl, pyridine or morpholine.

The compounds of the formula I can be employed as racemates or as enantiomerically pure compounds or as diastereomers. If enantiomerically pure compounds are desired, these can be obtained, for example, by carrying out a classical resolution with the compounds of the formula I or their intermediates using a suitable optically active base or acid.

The invention also relates to compounds which are mesomeric or tautomeric with compounds of the formula I, for example those in which the keto group of the formula I is present as an enol tautomer.

The invention further relates to the physiologically tolerable salts of the compounds I, which can be obtained by conversion of compounds I using a suitable acid or base.

The piperidineketocarboxylic acid derivatives I according to the invention can be prepared in various ways, which have been outlined in Schemes 1 and 2.

Starting from piperidinecarboxylic acids II, the derivative III is obtained by conversion under customary conditions using activated acid derivatives R1-L, L being a leaving group such as Cl, imidazole or N-hydroxybenzotriazole. This reaction is carried out in anhydrous, inert solvents such as methylene chloride, tetrahydrofuran or dimethylformamide at from −20 to +25° C. and is carried out as a rule under customary conditions as are summarized in Houben-Weyl, Methoden der organischen Chemie [Methods of Organic Chemistry], 4th Edition, E5, Chapter V.

The piperidinecarboxylic acid esters III are converted into the acids IV in aqueous medium or in mixtures of water and organic solvents such as alcohols or tetrahydrofuran at room temperature or elevated tempertures, such as 25–100° C., using acids or bases such as lithium hydroxide, sodium hydroxide or potassium hydroxide.

These acids IV are linked to an α-amino acid derivative, the customary conditions such as those above being used, which are listed in Houben-Weyl.

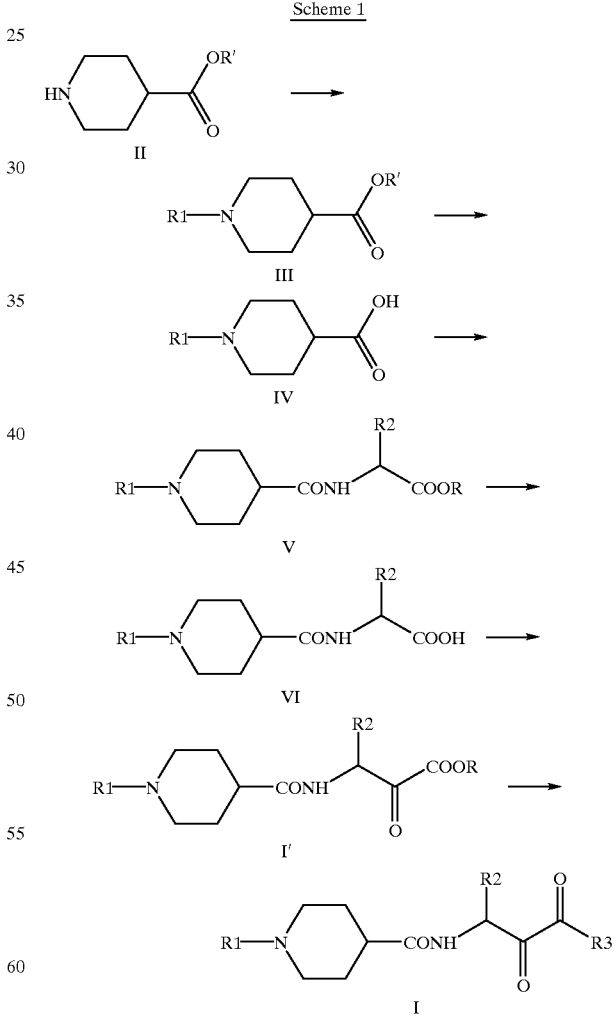

Scheme 1

The derivatives V, which as a rule are esters, are converted into the ketocarboxylic acids VI similarly to the hydrolysis described above. The ketoesters VII are prepared in a reaction similar to that of Dakin-West, the reaction being carried out according to a method of Zhaozhao Li et al. J. Med. Chem., 1993, 36, 3472–80. In this method, a carboxylic acid such as V's reacted with oxalic acid monoester chloride at elevated temperature (50–100° C.) in solvents such as tetrahydrofuran and the product thus obtained is then reacted with bases such as sodium ethoxide in ethanol at 25–80° C. to give the ketoester I' according to the invention. The ketoesters I' can be hydrolyzed, as described above, for example to give the ketocarboxylic acids according to the invention.

The reaction to give ketoamides I' is also carried out similarly to the method of Zhaozhao Li et al.(see above). The keto group in I' is protected at room temperature by addition of 1,2-ethanedithiol under Lewis acid catalysis, such as, for example, boron trifluoride etherate, in inert solvents, such as methylene chloride, a dithiane being obtained. These derivatives are reacted with amines $R^3$-H in polar solvents, such as alcohols, at 0–80° C., the ketoamides I' being obtained.

tions which have already been described. The alcohol derivative X can be oxidized again to give ketocarboxylic acid derivatives I according to the invention.

The ketone derivatives I contained in the present invention are inhibitors of cysteine proteases, in particular cysteine proteases such as the calpains I and II and cathepsins B and L.

The inhibitory action of the ketone derivatives I was determined using enzyme tests customary in the literature, where, as an activity scale, a concentration of the inhibitor was determined at which 50% of the enzyme activity is inhibited (=$IC_{50}$). The ketone derivatives I were in this way measured for inhibitory action on calpain I, calpain II and cathepsin B.

Cathepsin B test

The cathepsin B inhibition was determined similarly to a method by S. Hasnain et al., J. Biol. Chem. 1993, 268, 235–40.

2 μL of an inhibitor solution, prepared from inhibitor and DMSO (final concentrations: 100 μM to 0.01 μM) are added Scheme 2

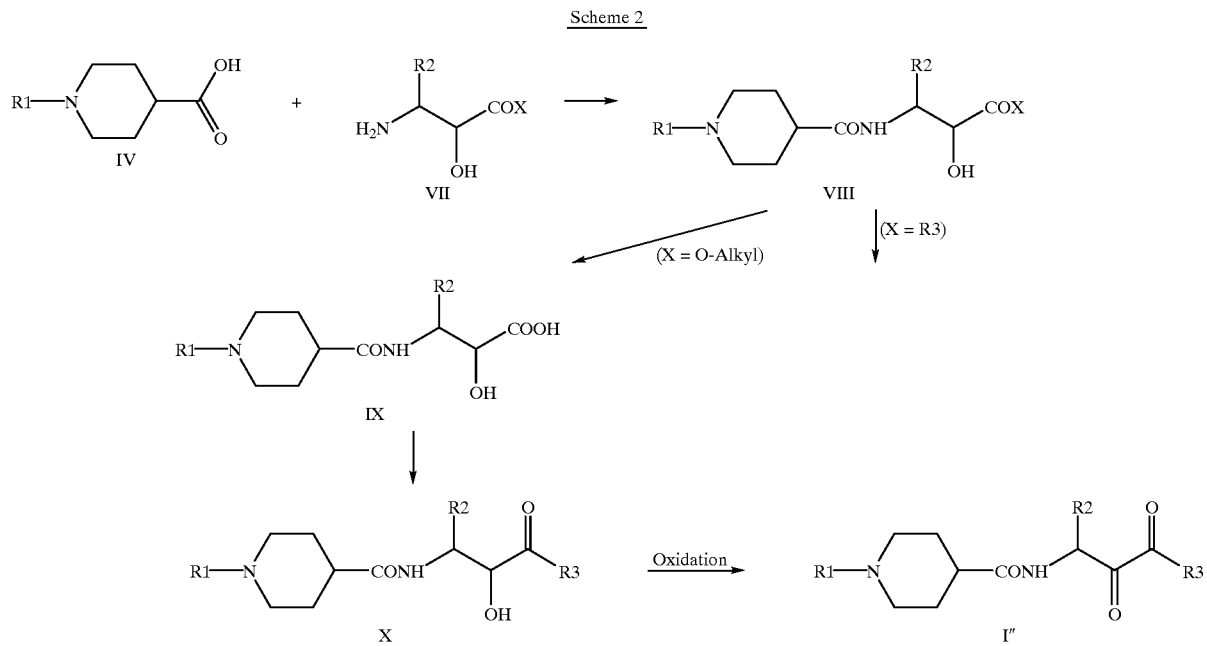

An alternative method is illustrated in Scheme 2. The piperidineketocarboxylic acids IV are reacted with aminohydroxycarboxylic acid derivatives VII (see S. L. Harbenson et al., J. Med. Chem. 1994, 37, 2918–29) under customary peptide coupling methods (see above, Houben-Weyl), amides VIII being obtained. These alcohol derivatives VIII can be oxidized to the ketocarboxylic acid derivatives I' according to the invention. For this, various customary oxidation reactions (see C. R. Larock, Comprenhensive [sic] Organic Transformations, VCH Publisher, 1989, page 604 et seq.) such as, for example, Swern oxidations and oxidations similar to those of Swern (T. T. Tidwell, Synthesis 1990, 857–70) or sodium hypochloride/TEMPO (S. L. Harbenson et al., see above) can be used.

When VIII are α-hydroxy esters (X=O-alkyl), these can be hydrolyzed to carboxylic acids IX, the reaction being carried out similarly to the above methods, but preferably using lithium hydroxide in water/tetrahydrofuran mixtures at room temperature. Other esters or amides X are prepared by reaction with alcohols or amines under coupling condito 88 μL of cathepsin B (cathepsin B from human liver (Calbiochem), diluted to 5 units in 500 mM buffer). This mixture is preincubated at room temperature (25° C.) for 60 minutes and the reaction is then started by addition of 10 μL of 10 mM Z-Arg-Arg-pNA (in buffer with 10% DMSO). The reaction is monitored at 405 nM in a microtiter plate reader for 30 minutes. The $IC_{50}$s are then determined from the maximum increases.

Calpain I and II test

The testing of the inhibitory properties of calpain inhibitors is carried out in buffer with 50 mM tris-HCl, pH 7.5; 0.1 M NaCl, 1 mM dithiotreithol [sic]; 0.11 mM $CaCl_2$, the fluorogenic calpain substrate Suc-Leu-Tyr-AMC (25 mM dissolved in DMSO, Bachem/Switzerland) being used (Sasaki et al. J. Biol. Chem. 1984, Vol. 259, 12489–12494). Human μ-calpain is isolated from erythrocytes following the methods of Croall and DeMartino (BBA 1984, Vol. 788, 348–355) and Graybill et al. (Bioorg. & Med. Lett. 1995, Vol. 5, 387–392). After several chromatographic steps (DEAE-Sepharose, phenyl-Sepharose, Superdex 200 and Blue Sepharose), the enzyme is obtained with a purity <95%, assessed according to SDS-PAGE, Western blot analysis and N-terminal sequencing. The fluorescence of the cleavage product 7-amino-4-methylcoumarin (AMC) is monitored in a Spex Fluorolog Fluorimeter at $\lambda_{ex}$=380 nm and $\lambda$em=460 nm. In a measuring range of 60 min, the cleavage of the substrate is linear and the autocatalytic activity of calpain is low when the experiments are carried out at temperatures of 12° C. (see Chatterjee et al., 1996, Bioorg. & Med. Chem. Lett., Vol. 6, 1619–1622). The inhibitors and the calpain substrate are added to the experimental mixture as DMSO solutions, where DMSO in the final concentration should not exceed 2%.

In a typical experimental mixture, 10 μl of substrate (250 μm final) and subsequently 10 μl of μ-calpain (2 μg/ml final, ie. 18 nM) are added to a 1 ml cuvette which contains buffer. The calpain-mediated cleavage of the substrate is measured for 15 to 20 min. Subsequent addition of 10 μl of inhibitor (50 to 100 μM solution of DMSO) and measurement of the inhibition of cleavage for a further 40 min. $K_i$ values are determined according to the customary equation for reversible inhibition, ie. $K:=I(v_0/v)-1$; where I=inhibitor concentration, $v_o$=initial rate before addition of the inhibitor; $v_i$=reaction rate at equilibrium.

Platelet test for Determining the Cellular Activity of Calpain Inhibitors

The calpain-mediated degradation of proteins in platelets was carried out as described by Zhao ZhaoLi [sic] et al., J. Med. Chem., 1993, 36, 3472–3480. Human platelets were isolated from fresh sodium citrate blood of donors and adjusted to $10^7$ cells/ml in buffer (5 mM Hepes, 140 mM NaCl and 1 mg/ml BSA, pH 7.3).

Platelets (0.1 ml) are preincubated for 5 minutes with 1 μl of various concentrations of inhibitors (dissolved in DMSO). Calcium ionophore A 23187 (1 μM in the test) and calcium (5 mM in the test) were then added and a further incubation of 5 minutes at 37° C. was carried out. After a centrifugation step, the platelets were taken up in SDS-Page sample buffer and heated at 95° C. for 5 minutes, and the proteins were separated in an 8% strength gel. The degradation of the two proteins actin-binding protein (ABP) and talin was monitored by quantitative densitometry, since after the addition of calcium and ionophore these proteins disappeared and a new band resulted in the region of 200 Kd molecular weight. The half-maximal enzyme activity is determined from this.

Glutamate-induced Cell Death of Cortical Neurones

The test was carried out as described by Choi D. W., Maulucci-Gedde M. A. and Kriegstein A. R. (1987) Glutamate neurotoxicity in cortical cell culture. *J. Neurosci.* 7, 357–368.

The halves of the cortex were dissected from 15-day-old mice embryos and the individual cells were obtained enzymatically (trypsin). These cells (glia und cortical neurones) are inoculated into 24 well plates. After three days (laminin-coated plates) or seven days (ornithine-coated plates) the mitosis treatment is carried out with FDU (5-fluoro-2-deoxyuridine. 15 days after cell preparation, cell death is induced by addition of glutamate (15 minutes). After the removal of glutamate, the calpain inhibitors are added. 24 hours later, the cell damage is ascertained by the determination of lactate dehydrogenase (LDH) in the cell culture supernatant.

It is postulated that calpain also plays a part in apoptotic cell death (M. K. T. Squier et al. J. Cell. Physiol. 1994, 159, 229–237; T. Patel et al. Faseb Journal 1996, 590, 587–597). Cell death with calcium in the presence of a calcium ionophore was therefore induced in a further model in a human cell line. Calpain inhibitors must pass into the cell and inhibit calpain there in order to prevent the induced cell death.

Calcium-mediated Cell Death in NT2 Cells

Cell death can be induced in the human cell line NT2 by calcium in the presence of the ionophore A 23187. $10^5$ cells/well were plated out in microtiter plates 20 hours before the experiment. After this period, the cells were incubated with various concentrations of inhibitors in the presence of 2.5 μM ionophore and 5 mM calcium. 0.05 ml of XTT (Cell Proliferation Kit II, Boehringer Mannheim) was added to the reaction mixture after 5 hours. The optical density is determined in the Easy Reader EAR 400 from SLT, according to the instructions of the manufacturer, after approximately 17 hours. The optical density at which half the cells have died is calculated from the two controls with cells without inhibitors, which were incubated in the absence and presence of ionophore.

The ketone derivatives I are inhibitors of cysteine proteases such as calpain I or II and cathepsin B or L and can thus be used for controlling illnesses which are associated with an increased enzyme activity of the calpain enzymes or cathepsin enzymes. The present ketone derivatives I can accordingly be used for the treatment of neurodegenerative diseases which occur after ischemia, trauma and massive hemorrhages, and of neurodegenerative diseases such as multiple infarct dementia, Alzheimer's disease and Huntington's disease and furthermore for the treatment of damage to the heart after cardiac ischemias, damage to the kidneys after renal ischemia, skeletal muscle damage, muscular dystrophy, damage which results due to proliferation of the smooth muscle cells, coronary vasospasm, cerebral vasospasm, cataracts of the eyes, and restenosis of the blood vessles after angioplasty.

Moreover, the ketone derivatives I can be useful in the chemotherapy of tumors and metastasis thereof and are used for the treatment of diseases in which an increased interleukin-1 level occurs, such as in inflammation and rheumatic disorders.

Beside the customary pharmaceutical auxiliaries, the pharmaceutical preparations according to the invention contain a therapeutically efficacious amount of the compounds I.

For local external use, for example in powders, ointments or sprays, the active compounds can be contained in the customary concentrations. As a rule, the active compounds are contained in an amount from 0.0001 to 1% by weight, preferably from 0.001 to 0.1% by weight.

In the case of internal use, the preparations are administered in individual doses. In an individual dose, from 0.1 to 100 mg are given per kg of body weight. The preparation can be administered in one or more doses daily, depending on the nature and severity of the disorders.

According to the desired manner of administration, the pharmaceutical preparations according to the invention contain the customary pharmaceutical excipients and auxiliaries in addition to the active compound. For local external use, it is possible to use pharmaceutical auxiliaries, such as ethanol, isopropanol, ethoxylated castor oil, ethoxylated hydrogenated castor oil, polyacrylic acid, polyethylene glycol, polyethylene glycostearate, ethoxylated fatty alcohols, liquid paraffin, petroleum jelly and wool fat. For internal use, for example, lactose, propylene glycol, ethanol, starch, talc and polyvinylpyrrolidone are suitable.

Antioxidants such as tocopherol and butylated hydroxyanisole and also butylated hydroxytoluene, flavor-improving additives, stabilizers, emulsifiers and lubricants can furthermore be contained.

The substances contained in the preparation in addition to the active compound and the substances used in the production of the pharmaceutical preparations should be toxicologically harmless and compatible with the respective active compound. The pharmaceutical preparations are prepared in a customary manner, for example by mixing the active compound with other customary excipients and diluents.

Pharmaceutical preparations are prepared by methods familiar to the person skilled in the art (see, for example, H. Sucker et al., Pharmazeutische Technologie, Thieme Verlag, Stuttgart, 1991).

The pharmaceutical preparations can be administered in various types of administration, for example, orally, parenterally, such as intravenously by infusion, subcutaneously, intraperitoneally and topically. Preparation forms such as tablets, emulsions, infusion and injection solutions, pastes, ointments, gels, creams, lotions, powders and sprays are thus possible.

EXAMPLES

Example 1

Ethyl 4-methyl-2-oxo-3(1-(E-3-phenyl-1-acryloyl) piperidin-4-yl)-amidovalerate

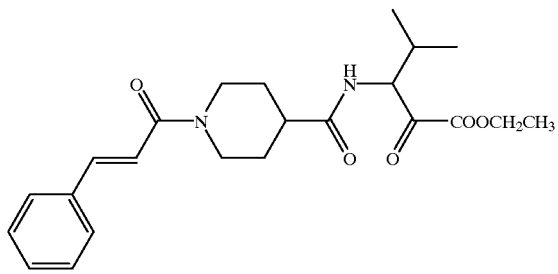

a) 1-(E-Phenyl-1-acryloyl)piperidinyl-4-carboxylic acid 32.0 g (0.248 mol) of piperidine-4-carboxylic acid were dissolved in 500 ml of pyridine and then treated in portions with 43.3g (0.26 mol) of cinnamoyl chloride. The whole was stirred at room temperature for 16 h. The reaction mixture was then concentrated under reduced pressure and the residue was partitioned between 2M hydrochloric acid and ethyl acetate. The organic phase was separated off, dried and concentrated in vacuo. 47.0 g (76%) of the product were obtained. M.p.: 178–179° C.

b) Methyl 4-methyl-2(1-(E-3-phenyl-1-acryloyl)-piperidin-4-yl)amido-butyrate 20.0 g (77.1 mmol) of the product 1a and 12.5 g (77.1 mmol) of L-valine methyl ester hydrochloride were added to 350 ml of methylene chloride and the mixture was treated dropwise with ice-cooling with 25.6 ml (185.1 mmol) of triethylamine. It was stirred for 1 h and 3.1 g (23.1 mmol) of 1-hydroxy-1H-benzotriazole (HOBT) were then added. The reaction mixture was cooled to 0° C. and then treated in portions with 14.8 g (77.1 mmol) of N'-(3-dimethylaminopropyl)-N-ethylcarbodiimide (EDC). The whole was stirred at room temperature for 16 h. [lacuna] organic phase was then washed with water, aqueous sodium hydrogen-carbonate solution, 5% strength citric acid solution and again with water, dried and concentrated under reduced pressure. 27.3 g (96%) of the product were obtained.

1H-NMR (CDCl$_3$): δ=0.9 (6H), 1.6–2.0 (3H), 2.2 (1H), 2.5 (1H), 2.8 (1H), 3.2 (1H), 3.8 (3H), 4.2 (1H), 4.6 (1H), 4.7 (1H), 6.0 (1H), 6.9 (1H), 7.3–7.6 (5H) and 7.6 (1H) ppm.

c) 4-Methyl-3(1-(E-3-phenyl-1-acryloyl)piperidin-4-yl) amidobutyric acid 27.0 g (72.5 mmol) of the product 1c were dissolved in 200ml of tetrahydrofuran and treated with 3.5 g (145 mmol) of lithium hydroxide dissolved in 250 ml of water. The whole was stirred at room temperature for 1 h. The tetrahydrofuran was then removed under reduced pressure and the resulting aqueous solution was extracted with ethyl acetate. This was then neutralized with 1M hydrochloric acid and extracted again with ethyl acetate. The latter organic phase was dried and concentrated under reduced pressure, 26 g (100%) of the product being obtained.

1H-NMR (CDCl$_3$): δ=1.0 (6H), 1.6–2.2 (6H), 2.5 (1H), 2.9 (1H), 3.2 (1H), 4.6 (2H), 6.4 (2H), 6.4 (1H), 6.9 (1H), 7.3–7.6 (5H) and 7.7 (1H) ppm.

d) Ethyl 4-methyl-2-oxo-3(1-(E-3-phenyl-1-acryloyl) piperidin-4-yl)amidovalerate 26.0 g (72.5 mmol) of the product 1c, 0.9 g (7.25 mmol) of 4-dimethylaminopyridine (DMAP) and 23.4 ml (0.29 mol) of pyridine were dissolved in 150 ml of anhydrous tetrahydrofuran. 16.2 ml (0.15 mol) of ethyl oxalyl chloride were then swiftly added dropwise so that the temperature rose to about 50° C. The whole was refluxed for a further 3 h. The reaction mixture was stirred at room temperature for 16 h. 100 ml of water were then cautiously added and the mixture was stirred again for about 30 minutes and partitioned between water and ethyl acetate. The organic phase was washed again several times with water, dried and concentrated under reduced pressure.

The enol ester thus obtained was dissolved in 200 ml of ethanol and treated with 0.47 g (5.6 mmol) of potassium ethoxide, and the mixture was stirred at room temperature for 16 h. The whole was then concentrated under reduced pressure and the residue was purified by chromatography (eluent: methylene chloride/methanol=20/1), 10.8 g (36%) of the product being obtained.

MS (FAB): m/e=414 (M$^+$).

Example 2

4-Methyl-2-oxo-3(1-(E-3-phenyl-1-acryloyl)piperidin-4-yl)amidovaleramide

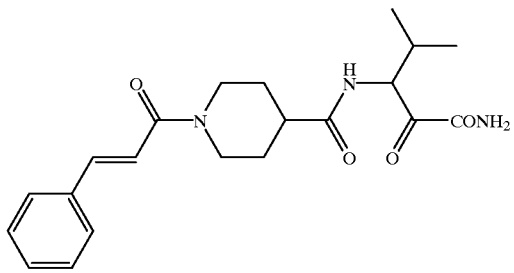

a) Ethyl 2,2-ethylenedimercapto-4-methyl-E-3-(1-(3-phenyl)-1-acryloyl)piperidin-4-yl)amidovalerate 6.0 g (14.6 mmol) of the product 1d and 1.5 ml (17.5 mmol of 1,2-ethanedithiol were dissolved in 20 ml of anhydrous methylene chloride and the mixture was treated with 4 ml of boron trifluoride etherate. The whole was stirred at room temperature for 16 h. The reaction mixture was then diluted with 10 ml of methylene chloride and washed 3x with saturated sodium chloride solution. The organic phase was dried and concentrated under reduced pressure, 7.3 g of a crude product being obtained, which was reacted further in unpurified form.

b) 4-Methyl-2-oxo-3-(E-1(3-phenyl)-1-acryloyl) piperidin-4-yl)amidovaleramide 1.7 g (3.6 mmol) of the product 2a were introduced into 20 ml of 2 M ethanolic ammonia solution and the mixture was stirred at room temperature for 16 h. The whole was then concentrated under reduced pressure and the residue was purified by chromatography (eluent:methylene chloride/ methanol=40/3), 0.22 g of the product being obtained.

MS (FAB): m/e=385 (M+).

Example 3

N-Ethyl-4-methyl-2-oxo-3(1-(E-3-phenyl-1-acryloyl) piperidin-4-yl)amidovaleramide

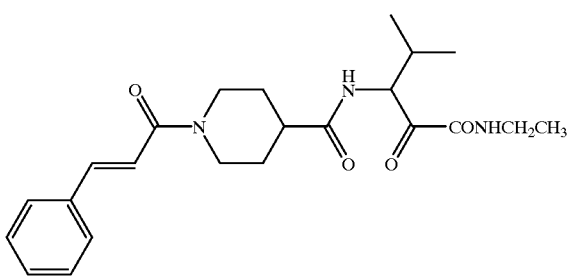

1.7 g (3.6 mmol) of the product 2a were reacted in ethanolic ethylamine solution similarly to procedure 2b, 0.15 g of the product being obtained.

MS (FAB): m/e=413 (M+).

Example 4

4-Methyl-N-(3-(morpholino-1-yl)propyl)-2-oxo-3(1-(E-3-phenyl-1-acryloyl)piperidin-4-yl)amidovaleramide

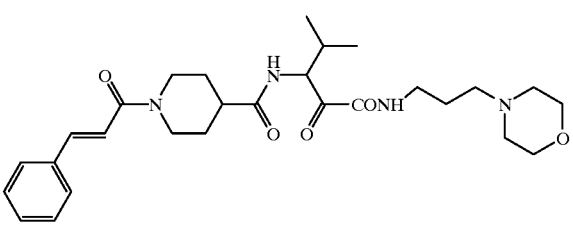

1.3 g (3.6 mmol) of the product 2a and 0.8 g (5.4 mmol) of 3-(morpholino-1-yl)propylamine were reacted similarly to procedure 2b and 1.1 g of the product were obtained.

MS (FAB): m/e=512 (M+).

Example 5

4-Methyl-2-oxo-3(1-(E-3-phenyl-1-acryloyl)piperidin-4-yl)-amido-N-(2-(pyrid-2-yl)ethyl)valeramide

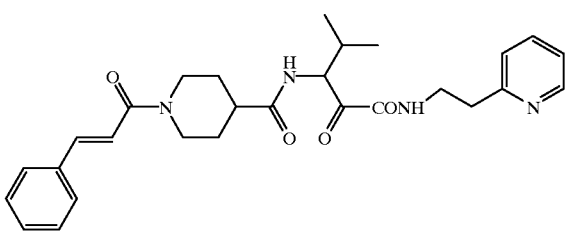

1.3 g (2.8 mmol) of the product 2a and 0.7 g (5.5 mmol) of 2-(2-aminoethyl)pyridine were reacted similarly to procedure 2b and 0.85 g of the product was obtained.

MS (FAB): m/e=490 (M+).

Example 6

Ethyl 2-oxo-4-phenyl-3(1-(E-3-phenyl-1-acryloyl)piperidin-4-yl)amidobutyrate

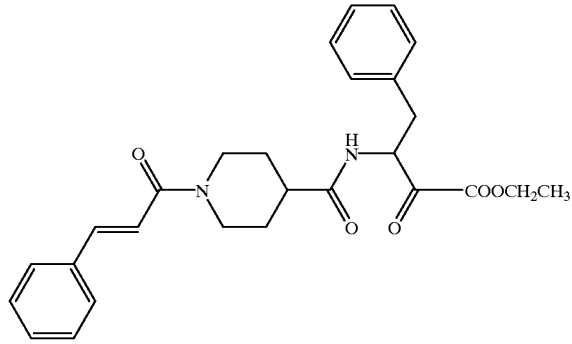

a) Methyl 3-phenyl-3(1-(E-3-phenyl-1-acryloyl) piperidin-4-yl)amidopropionate

The product was prepared from the intermediate 1a and phenylalanine methyl ester similarly to procedure 1b.

1H-NMR (CDCl$_3$): δ=1.6–2.0 (3H), 2.35 (1H), 2.9 (1H), 3.0–3.3 (4H), 3.7 (3H), 4.1 (1H), 4.6 (1H), 4.9 (1H), 5.9 (1H), 6.9 (1H), 7.1 (2H) and 7.2–7.7 (9H) ppm.

b) 3-Phenyl-3(1-(E-3-phenyl-1-acryloyl)piperidin-4-yl) amidopropionic acid

The product was prepared from the intermediate 6a similarly to procedure 1c.

1H-NMR (CDCl$_3$): δ=1.4–2.0 (4H), 2.3 (1H), 2.8 (1H), 3.0–3.4 (3H), 4.0 (1H), 4.6 (1H), 4.9 (1H), 4.9 (1H), 6.2 (1H), 6.8 (1H), 7.0–7.8 (11H) and about 8.2 (broad) ppm.

c) Ethyl 2-oxo-4-phenyl-3(1-(E-3-phenyl-1-acryloyl) piperidin-4-yl)amidobutyrate The product was prepared from the intermediate 6b similarly to procedure 1d.

MS (FAB): m/e=462 (M+).

Example 7

N-(3-(Morpholin-1-yl)propyl)-2-oxo-4-phenyl-3(1-(E-3-phenyl-1-acryloyl)piperidin-4-yl)amidobutyramide

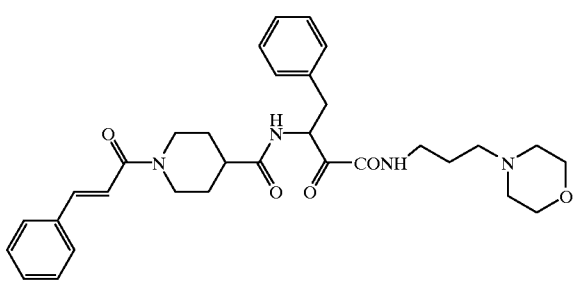

The product was prepared from Example 6 and 1-(3-aminopropyl)-morpholine similarly to procedure 2b.

1H-NMR (CDCl$_3$): δ=1.4–1.9 (6H), 2.3–2.6 (6H), 2.8 (1H), 2.2 (2H), 2.3–2.5 (3H), 2.6–2.8 (4H), 4.1 (1H), 4.6 (1H), 5.5(1H), 6.1 (1H), 6.9 (1H), 7.1 (1H), 7.2–7.7(10H) and 8.9 (1H) ppm.

Example 8

2-Oxo-4-phenyl-3(1-(E-3-phenyl-1-acryloyl)piperidin-4-yl)amidobutyramide

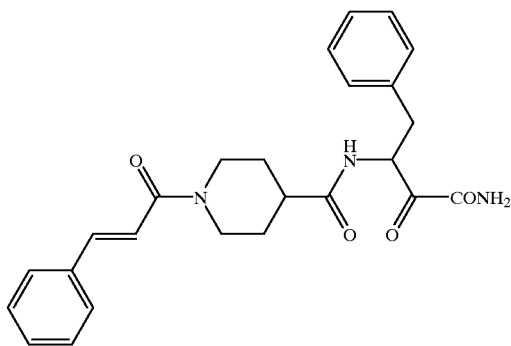

The product was prepared from Example 6 and ethanolic ammonia solution similarly to procedure 2b.

1H-NMR (D$_6$-DMSO):=1.2–1.9 (4H), 2.4 (1H), 2.7–2.9 (2H), 3.0–3.2 (2H), 4.1–4.3 (3H), 5.1 (1H) and 7.0–8.2 (14 H) ppm.

Example 9

4-Methyl-N(2-(morpholin-1-yl)ethyl)-2-oxo-3(1-(E-3-phenyl-1-acryloyl)piperidin-4-yl)amidovaleramide

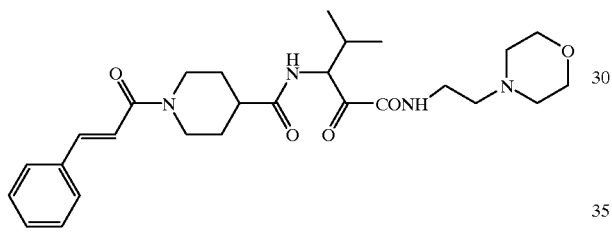

The product was prepared from the intermediate 2a and 1-(2-aminoethyl)morpholine similarly to procedure 2b.
MS: m/e=498 (M$^+$).

Example 10

Ethyl 2-oxo-3(1-(E-3-phenyl-1-acryloyl)piperidin-4-yl)amidovalerate

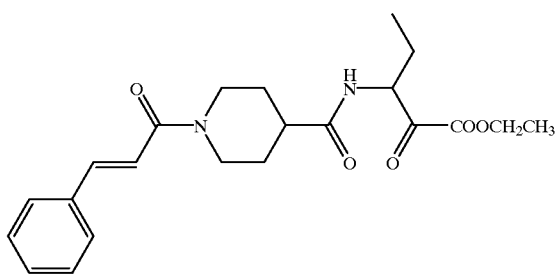

a) Ethyl 3(1-(E-3-phenyl-1-acryloyl)piperidin-4-yl)amidobutyrate

The product was prepared from the intermediate 1a and methyl 2-aminobutyrate similarly to procedure 1b.

1H-NMR (CDCl$_3$): δ=0.9 (3H), 1.6–2.0 (6H), 2.5 (1H), 2.9 (1H), 3.2 (1H), 3.8 (3H), 4.2 (1H), 4.5–4.7 (2H), 6.3 (1H), 6.9 (1H), 7.4 (3H), 7.6 (2H) and 7.7 (1H) ppm.

b) 3(1-(E-3-Phenyl-1-acryloyl)piperidin-4-yl)amidobutyric acid

The product was prepared from the intermediate 10a similarly to procedure 1c.

1H-NMR (D$_6$-DMSO): δ=0.9 (3H), 1.3–1.9 (6H), 2.6 (1H), 2.7 (1H), 3.1 (1H), 4.1 (1H), 4.3 (1H), 4.5 (1H), 7.2–7.6 (5H), 7.7(2H), 8.0 (1H) and 12.5 (broad) ppm.

c) Ethyl 2-oxo-3(1-(E-3-phenyl-1-acryloyl)piperidin-4-yl)amidovalerate

The product was prepared from the intermediate 10b similarly to procedure 1d.

1H-NMR (CDCl$_3$): δ=0.9 (3H), 1.4 (3H), 1.8–2.2 (6H), 2.5 (1H), 2.8 (1H), 3.2 (1H), 4.2 (1H), 4.4 (2H), 4.6 (1H), 5.1 (1H), 6.7 (1H), 6.9 (1H), 7.4 (3H), 7.5 (2H) and 7.7 (1H) ppm.

Example 11

2-Oxo-3(1-(E-3-phenyl-1-acryloyl)piperidin-4-yl)amidovaleramide

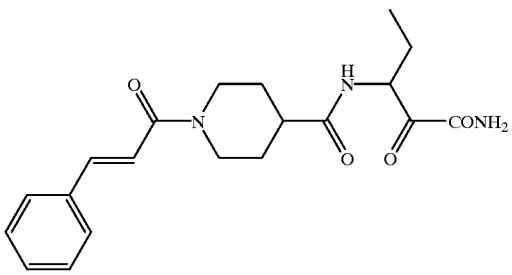

The product was prepared from the product 10 and ethanolic ammonia solution similarly to procedures 2a and b.

MS: m/e=371 (M$^+$).

Example 12

Ethyl 3(1-(2-naphthylsulfonyl)piperidin-4-yl)amido-2-oxo-4-phenylbutyrate

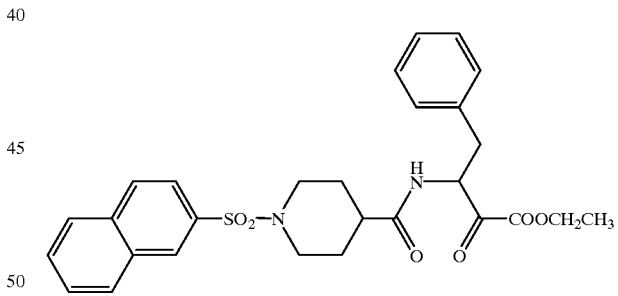

a) 1-(2-Naphthylsulfonyl)piperidine-4-carboxylic acid 26.0 g (0.2 mol) of piperidine-4-carboxylic acid were dissolved in 250 ml of pyridine and the solution was treated with 47.6 g (0.2 mol) of 2-naphthylsulfonyl chloride in portions at room temperature. The whole was stirred at room temperature for about 5 h. The reaction mixture was concentrated under reduced pressure and the residue was partitioned between ethyl acetate and 2 M hydrochloric acid. The organic phase was dried and concentrated under reduced pressure. 48.5 g (75%) of the product were obtained.

b) Ethyl 3(1-(2-naphthylsulfonyl)piperidin-4-yl)amido-2-oxo-4-phenylpropionate

The product was prepared from the intermediate 12a similarly to procedure 1b.

1H-NMR (D$_6$DMSO): δ=1.1 (3H), 1.4–1.8 (5H), 2.3–2.6 (2H), 2.7–3.2 (3H), 3.5–3.8 (2H), 4.0 (2H), 4.5 (1H), 7.2 (4H), 7.7(3H), 8.1–8.3(3H) and 8.5 (1H) ppm.

c) 3(1-(2-Naphthylsulfonyl)piperidin-4-yl)amido-2-oxo-4-phenyl-propionic acid

The product was prepared from the intermediate 12b similarly to procedure 1c.

1H-NMR (D$_6$-DMSO): δ=1.3–1.8 (5H), 2.3–2.6 (3H), 2.8–3.2(2H), 3.4–3.8 (2H), 4.4 (1H), 7.2 (4H), 7.7 (3H), 8.0–8.3 (4H) and 8.4 (1H) ppm.

d) Ethyl 3(1-(2-naphthylsulfonyl)piperidin-4-yl)amido-2-oxo-4-phenylbutyrate

The product was prepared from the intermediate 12c similarly to procedure 1d.

1H-NMR (D$_6$-DMSO) δ=1.2 (3H), 1.3–1.9 (4H), 2.2 (1H), 2.3–2.5 (2H), 2.8 (1H), 3.1 (1H), 3.6 (2H), 4.2 (2H), 4.4(1H), 7.0–7.3 (5H), 7.7 (3H), 8.0–8.3 (3H) and 8.4 (2H) ppm.

Example 13

3(1-(2-Naphthylsulfonyl)piperidin-4-yl)amido-2-oxo-4-phenylbutyramide

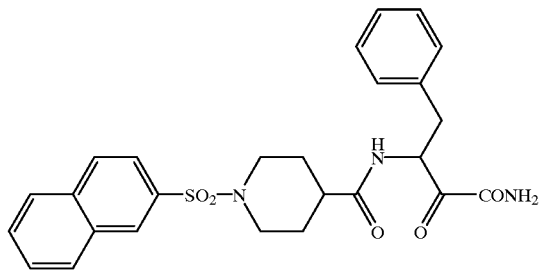

The product was prepared from Example 12 similarly to procedures 2a and b.

MS (FAB): m/e=493 (M$^+$).

Example 14

5N-(3-(Morpholin-1-yl)pop-1-yl)-3(1-(2-naphthylsulfonyl)-piperidin-4-yl)amido-2-oxo-4-phenylbutyramide

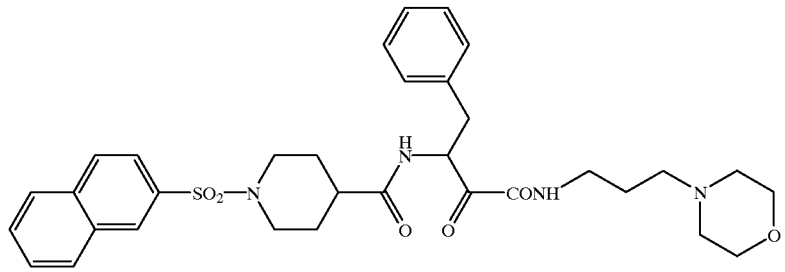

The product was prepared from the product 12 and 1-(3-aminoprop-1-yl)morpholine similarly to procedures 2a and b.

MS (FAB): m/e=620 (M$^+$).

Example 15

3(1-(2-Naphthylsulfonyl)piperidin-4-yl)amido-2-oxo-4-phenyl-N(2-(2-pyridyl)ethyl)butyramide

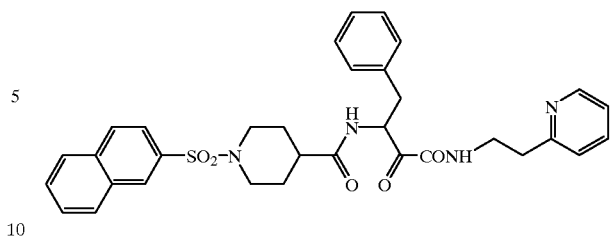

The product was prepared from Example 12 and 2-(2-aminoethyl)-pyridine similarly to procedures 2a and b.

MS (FAB): m/e=598 (M$^+$).

Example 16

3(S)-(1-(2-Naphthoyl)piperidin-4-yl)amido-2-oxo-4-phenylbutyramide

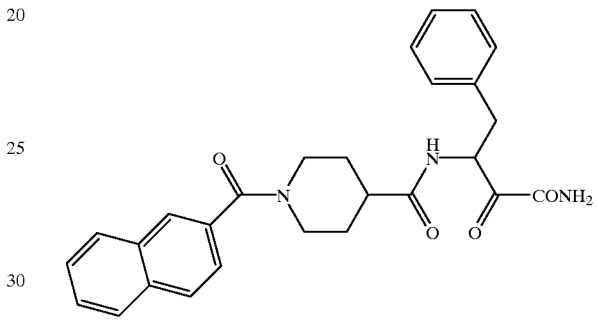

a) 3(S)-(N-tert-Boc-amino)-2(R,S)-hydroxy-4-phenylbutyramide 17.7 g (60 mmol) of 3(S)-(N-tert-Boc-amino)-2-(R,S)-hydroxy-4-phenylbutyric acid (S. L. Harenson et al., J. Med. Chem. 1994, 37, 2918–29) and 8.1 g (60 mmol) of 1-hydroxybenzotriazole were dissolved in 150 ml of anhydrous dimethylformamide. 12.6 g (66 mmol) of N'-(3-dimethylaminopropyl)-N-ethylcarbodiimide hydrochloride and 48 ml (about 2 molar) of ethanolic ammonia solution were added in succession at −50° C. and the mixture was stirred at this temperature for about 1 h. It was then stirred for about a further 16 h at room temperature. 500 ml of water were then added and the whole was extracted with ethyl acetate. The organic phase was washed with dilute sodium hydroxide solution and water, dried and concentrated under reduced pressure. The residue was additionally treated with n-heptane and the resulting precipitate was filtered off with suction. 13.5 g (76%) of the product were obtained.

1H-NMR (D$_6$-DMSO): δ=1.3 (9H), 2.6–2.9 (2H), 3.7 (1H), 5.7(1H), 6.2(1H) and 7.3 (5H) ppm.

b) 3(S)-Amino-2(R,S)-hydroxy-4-phenylbutyramide 13.4 g (46 mmol) of the compound 17a were dissolved in 300 ml of methylene chloride and treated with 100 ml of trifluoroacetic acid. The whole was stirred at room temperature for 1 h and then concentrated under reduced pressure. The residue was partitioned between water and ether and the aqueous phase was then concentrated under reduced pressure. 12.3 g (88%) of the product were obtained as trifluoroacetate.

c) 2-(R,S)-Hydroxy-3(S)-(1-(2-naphthoyl)piperidin-4-yl)-amido-4-phenylbutyramide 1.1 g (3.6 mmol) of the compound 17b were reacted with 1.0 g (3.6 mmol) of 1-(2-naphthoyl)piperidine-4-carboxylic acid similarly to procedure 17a. 1.0 g (61%) of the product was obtained.

1H-NMR ($D_6$-DMSO): δ=1.2–1.9 (6H), 2.6–3.2 (4H), 3.6 (1H), 3.7–4.0(1H), 4.0(1H), 4.2–4.6(2H), 5.8 (1H) and 7.0–8.2 (14H) ppm.

d) 3(S)-(1-(2-Naphthoyl)piperidin-4-yl)amido-2-oxo-4-phenylbutyramide 0.46 g (1 mmol) of compound 17c and 0.4 g (4 mmol) of triethylamine were dissolved in 10 ml of dimethyl sulfoxide and the solution was treated at room temperature with 0.48 g (3 mmol) of sulfur trioxide-pyridine complex, dissolved in 5 ml of dimethyl sulfoxide. The whole was stirred for 16 h. 150 1 of water were then added and the precipitate was filtered of with suction. 0.33 g (72%) of the product was obtained.

MS: m/e=457 ($M^+$).

The following examples of the general formula I can be prepared by the method mentioned in Example 16:

| Example No. | R$^1$ | R$^2$ | R$^3$ |
|---|---|---|---|
| 17 | 3,4-dimethoxybenzoyl | $CH_2CH_3$ | $NH_2$ |
| 18 | 3,4-dimethoxybenzoyl | $CH_2Ph$ | $NH_2$ |
| 19 | 3,4-dimethoxybenzoyl | $CH_2Ph$ | $NHCH_2CH_2CH_2$-morpholinyl |
| 20 | quinoline-3-carbonyl | $CH_2CH_2CH_3$ | $NH_2$ |
| 21 | quinoline-3-carbonyl | $CH_2CH_3$ | $NH_2$ |
| 22 | quinoline-3-carbonyl | $CH_2Ph$ | $NH_2$ |

-continued
| Example No. | R¹ | R² | R³ |
|---|---|---|---|
| 23 | 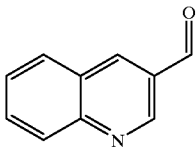 | CH₂Ph | NHCH₂CH₂CH₂— |
| 24 | 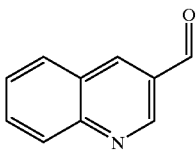 | CH₂Ph | NHCH₂CH₃ |
| 25 | 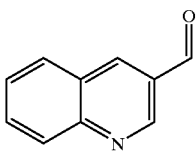 | CH₂Ph | NHCH₂CH₂— |
| 26 | 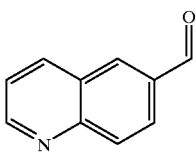 | CH₂— | NHCH₂CH₂— |
| 27 | 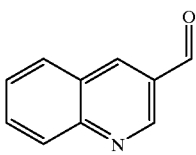 | CH₂— | NH₂ |
| 28 | 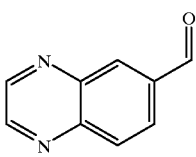 | CH₂Ph | NH₂ |
| 29 | 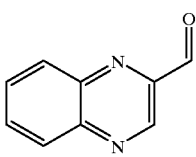 | CH₂Ph | NH₂ |
| 30 | 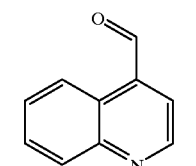 | CH₂Ph | NH₂ |
| 31 | 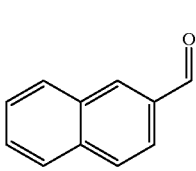 | CH₂Ph | NH₂ |

-continued

| Example No. | R¹ | R² | R³ |
|---|---|---|---|
| 32 | 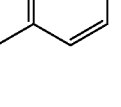 | CH₂Ph | CONH₂ |
| 33 | 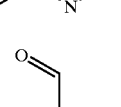 | CH₂Ph | CONH₂ |
| 34 | 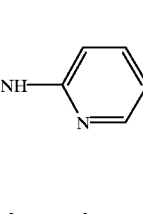 | CH₂Ph | CONH₂ |
| 35 | 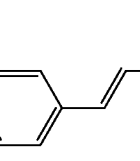 | CH₂Ph | CONH₂ |
| 36 |  | CH₂Ph | CONH₂ |
| 37 | 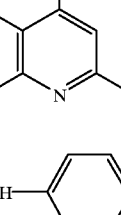 | CH₂Ph | CONH₂ |

We claim:

1. A piperidineketocarboxylic acid compound of the formula I

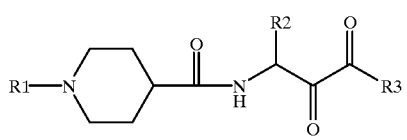

or its tautomeric and isomeric forms, or physiologically tolerable salts thereof, where the variables have the following meanings:

$R^1$ is —CO—$R^4$, —SO$^2$—$R^4$, —CONH—$R^4$, —COOR$^4$, —C(=N)—$R^4$, —C(=O)—NHR$^4$ and —C(=S)—NHR$^4$;

$R^2$ is —C$_1$–C$_6$-alkyl, which is branched or unbranched and can additionally carry a phenyl, pyridine or naphthyl ring which in turn can be substituted by at most two radicals $R^5$ selected from the group consisting of C$_1$–C$_4$-alkyl which is branched or unbranched, —O—C$_1$–C$_4$-alkyl, OH, Cl, F, Br, I, CF$_3$, NO$_2$, NH$_2$, CN, COOH, COO—C$_1$–C$_4$-alkyl, —NHCO—C$_1$–C$_4$-alkyl, —NHCOPh, —NHSO$_2$—C$_1$–C$_4$-alkyl, NHSO$_2$—Ph, —SO$_2$—C$_1$–C$_4$-alkyl and —SO$_2$Ph;

$R^3$ is —OR$^6$ and —NHR$^6$;

$R^4$ is —C$_1$–C$_6$-alkyl which is branched or unbranched, and in which optionally a chain of two or more C atoms may contain a double bond or triple bond and be substituted by one or two rings selected from the group consisting of phenyl, naphthalene, quinoxaline, quinoline, isoquinoline, pyridine, thiophene, benzothiophene, benzofuran, pyrimidine, thiazole, isothiazole, triazole, imidazole, cyclohexyl, cyclopentyl, fluorene, indole, benzimidazole, oxazole, isooxazole and furan, said rings optionally including up to two radicals $R^5$;

$R^6$ is hydrogen, a phenyl ring which can additionally carry one or two radicals $R^5$, C$_1$–C$_6$-alkyl which is branched or unbranched and can contain a double bond or a triple bond, and a ring such as phenyl, naphthalene, pyridine, pyrimidine, piperidine, pyrrolidine, morpholine, thiophene, quinoline and isoquinoline, said rings optionally carrying at most two radicals —NR$^7$R$^8$ or R⁵, R⁷ and R⁸ independently of one another being hydrogen or $C_1$–$C_6$-alkyl which is branched or unbranched.

2. A piperidineketocarboxylic acid compound of the formula I as claimed in claim 1, where $R^1$ is —C(=O)R⁴, —SO₂R⁴, $R^2$ is —$C_1$–$C_6$-alkyl, which is branched or unbranched, —CH₂—Ph or —CH₂-pyridyl, $R^3$ is —OR⁶ or —NHR⁶ and $R^4$, $R^5$ and $R^6$ have the meanings as set forth in claim 1.

3. A piperidineketocarboxylic acid compound of the formula I as claimed in claim 1, where $R^1$ is —C(=O)R⁴, —SO₂R⁴, $R^2$ is —$C_1$–$C_4$-alkyl or —CH₂— phenyl, $R^3$ is —NHR⁶, $R^4$ is —CH=CH—R⁹, it being possible for R⁹ to be a phenyl, naphthalene or quinoline, and $R^6$ is hydrogen or $C_1$–$C_4$-alkyl optionally substituted by phenyl, pyridine or morpholine.

4. A method of treating diseases caused by elevated calpain activity which comprises administrating to a patient in need thereof an effective amount of a compound as defined in claim 1.

5. A method of treating diseases caused by elevated calpain activity which comprises administrating to a patient in need thereof an effective amount of a compound as defined in claim 2.

6. A method of treating diseases caused by elevated calpain activity which comprises administrating to a patient in need thereof an effective amount of a compound as defined in claim 3.

7. A method of treating neurodegenerative diseases and neuronal injuries in a patient in need thereof which comprises administering to said patient an effective amount of a compound as defined in claim 1.

8. A method of treating neurodegenerative diseases and neuronal injuries in a patient in need thereof which comprises administering to said patient an effective amount of a compound as defined in claim 2.

9. A method of treating neurodegenerative diseases and neuronal injuries in a patient in need thereof which comprises administering to said patient an effective amount of a compound as defined in claim 3.

10. A method of treating neurodegenerative diseases and neuronal injuries which are casued by ischemia, trauma or massive hemorrhages which comprises administrating to a patient in need thereof an effective amount of a compound as defined in claim 1.

* * * * *